United States Patent [19]

Sturrock

[11] Patent Number: Plant 5,711

[45] Date of Patent: Apr. 8, 1986

[54] **DISTINCT VARIETY OF *PINUS RADIATA***

[76] Inventor: Lorie Sturrock, 6700 N. San Dimas Canyon Rd., San Dimas, Calif. 91773

[21] Appl. No.: 632,548

[22] Filed: Jul. 19, 1984

[51] Int. Cl.[4] ..... A01H 5/12

[52] U.S. Cl. ..... Plt./50

[58] Field of Search ..... Plt./50

*Primary Examiner*—Robert E. Bagwill

*Attorney, Agent, or Firm*—Flehr, Hohbach, Test, Albritton & Herbert

[57] ABSTRACT

A new and distinct variety of *Pinus radiata.* A newly found seedling that has a high branching frequency, superior growth vigor, an extensively developed root system, and primary and secondary needles extending over the entire length of all twigs and branches.

2 Drawing Figures

This invention relates to a new and distinct variety of *Pinus radiata* herein referred to as the new variety "Edward." "Edward" was discovered by Mrs. Lorie Sturrock as a new seedling on the Christmas Tree Farm of Bob and Lorie Sturrock located at 6700 North San Dimas Canyon Road, Sam Dimas, Calif.

"Edward" was found growing in a cultivated bed containing six to eight thousand seedlings of the "Monterey" variety of *Pinus radiata.* This cultivated bed was grown from seed originally planted in pots during December 1978 or January 1979. The seedlings were transferred to the cultivated bed during January 1980. "Edward" was first recognized as a new and distinct variety during October 1980 when it was observed that, unlike the "Monterey" variety, "Edward" did not require shearing to promote branching. Other characteristics of "Edward" which distinguish it from the "Monterey" variety will be described in more detail hereinafter.

At the request of Mrs. Sturrock, "Edward" was asexually propagated from terminal and lateral cuttings by Dr. William Libby at the University of California at Berkeley during January or February 1983.

Figure 1:
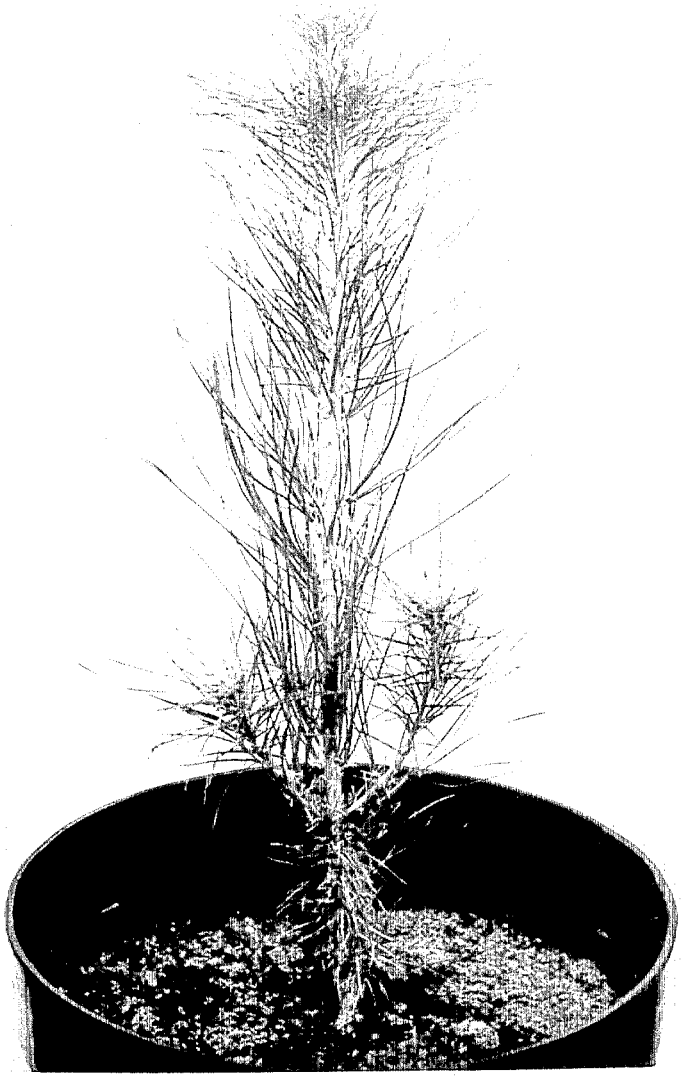

FIG. 1 is a color photograph of one of the seedlings taken during February 1984. It is approximately fifteen inches in height.

Plants of this new and distinct variety have not been offered for sale or described in any printed publication.

"Edward" demonstrates a number of characteristics which distinguish it from the "Monterey" variety of *Pinus radiata:*

Figure 2:
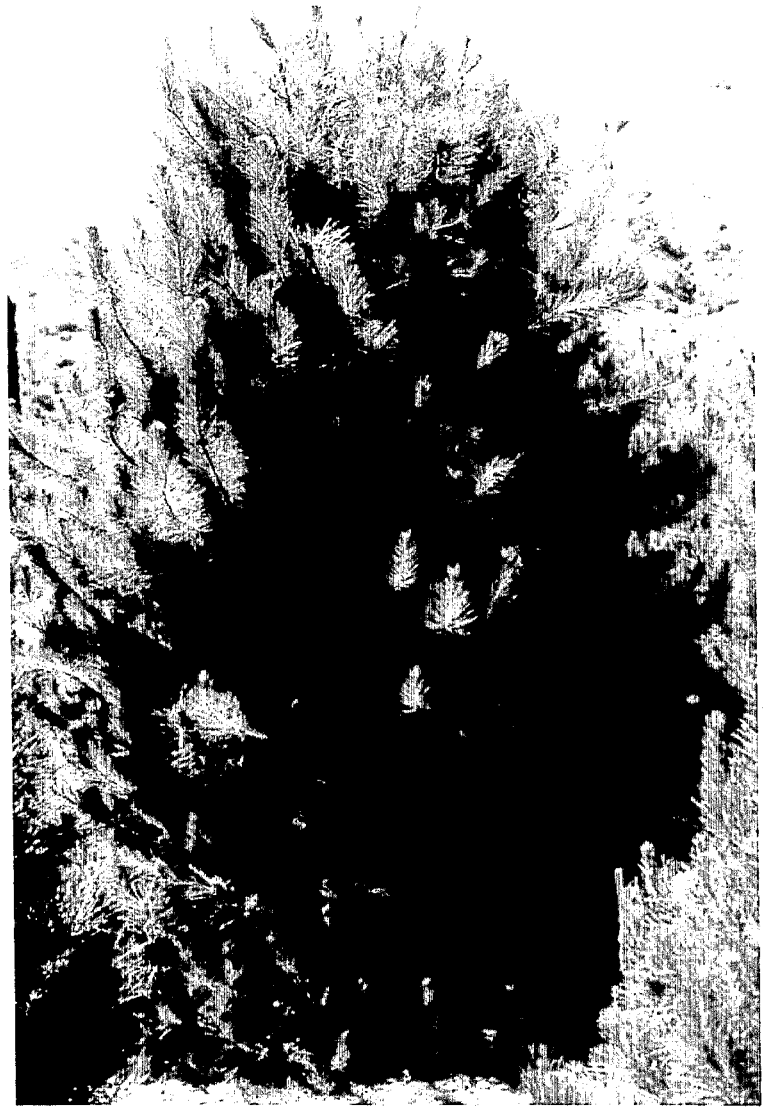

1. "Edward" has a high branching frequency. Unlike the "Monterey" variety, "Edward" does not require shearing to promote branching. The "Monterey" variety typically produces whorls separated by about twelve to twenty inches. The leader must be cut when it is about nine inches to produce whorls at ten to eleven inches. "Edward" does not require such treatment. As such, "Edward" has a full pyramidal form with little or no need for shearing. However, if sheared, "Edward" responds with many new branch shoots. FIG. 2 is a color photograph of the original "Edward" taken in April 1984. When this photograph was taken several hundred cutting had already been taken from "Edward" on two separate occasions. The first occasion was in January or February 1983 and the second was approximately one year later. As a consequence, this photograph does not accurately depict a mature unsheared "Edward" but does demonstrate the increase in branching frequency upon shearing.

2. "Edward" produces long primary and typical secondary needles. In the original "Edward" the needles are approximately six and one-eighth inches long whereas in a "Monterey" variety one to two years older than "Edward" the needles are about four and seven-eighths inches long. "Edward's" needles extend over the entire length of all twigs and branches and retain their color and viability. This characteristic in combination with "Edward's" high branching frequency results in a high density of foliage without the need to shear. In the "Monterey" variety brown bracts replace the branch needles along approximately the lower one-third of the branches.

3. "Edward" demonstrates an above average growth vigor as compared to the "Monterey" variety. The original "Edward" variety was planted just over five years ago and is currently about eleven and one-half feet tall and has a spread of about seven and one-half feet at its base. When grown for use as a Christmas tree, the "Monterey" variety typically requires five to six years of growth. "Edward," on the other hand, is estimated to require only three to four years to achieve the same size. The trunk circumference of "Edward" is about twenty-two inches at its base whereas a Monterey variety one or two years older than "Edward" has a trunk circumference of only eighteen and one-quarter inches.

4. Seedlings of "Edward" have a root system which is extensively developed when compared to seedlings of the "Monterey" variety of comparable age.

The above characteristics may be the consequence of a mutation which has imparted persistent juvenile growth characteristics to "Edward." Other less definite characteristics include possible resistance to smog damage and possible resistance to infection by oak root fungus.

The following is a detailed description of the new and distinct variety:

Locality where grown and observed: 6700 North San Dimas Canyon Road, San Dimas, Calif.

Parentage: *Pinus radiata* of uncertain origin.

Growth habit: Symmetrical conifer with year round growth.

Shape: Full pyramidal.

Size: Height is about $11\frac{1}{2}$ feet; spread at base about $7\frac{1}{2}$ feet.

Growth: High branching frequency and above average growth vigor, especially in vertical growth rate.

Foliage: Needles approximately $6\frac{1}{8}$ inches in length which maintain color and viability over entire extent of twigs and branches.

Roots: Extensively developed.

Seeds: None observed.

Propagation: Facile asexual reproduction from terminal and lateral cuttings.

Resistance: May be resistant to smog damage and infection by oak root fungus.

We claim:

1. A new and distinct variety of *Pinus radiata* substantially as herein shown and described, characterized particularly by its high branching frequency, needle distribution, above average growth vigor and extensively developed root system.

* * * * *